United States Patent [19]

White, Jr.

[11] 4,169,093

[45] Sep. 25, 1979

[54] 2-AMINO-5-PHENYLMETHOXY-6-METHOXYBENZOTHIAZOLE HYDROCHLORIDE

[75] Inventor: Ralph L. White, Jr., Norwich, N.Y.

[73] Assignee: Morton-Norwich Products, Inc., Norwich, N.Y.

[21] Appl. No.: 909,216

[22] Filed: May 25, 1978

[51] Int. Cl.² ........................................... C07D 277/62
[52] U.S. Cl. ................................... 548/164; 424/270
[58] Field of Search .......................................... 260/305

[56] References Cited

U.S. PATENT DOCUMENTS

| | | | |
|---|---|---|---|
| 3,706,759 | 12/1972 | Alaimo et al. | 260/305 |
| 3,714,177 | 1/1973 | Engelhart | 260/305 |
| 4,052,379 | 10/1977 | Gourley | 260/305 |

*Primary Examiner*—Nicholas S. Rizzo
*Attorney, Agent, or Firm*—Anthony J. Franze

[57] ABSTRACT

The compound 2-Amino-5-phenylmethoxy-6-methoxybenzothiazole hydrochloride is useful as an antifungal agent.

1 Claim, No Drawings

2-AMINO-5-PHENYLMETHOXY-6-METHOXYBENZOTHIAZOLE HYDROCHLORIDE

This invention relates to the compound 2-amino-5-phenylmethoxy-6-methoxybenzothiazole hydrochloride. This compound possesses antifungal activity. It is particularly inimical to the growth of *Microsporum canis* and *Aspergillus niger* in the commonly employed in vitro technique for determining antifungal activity at a concentration of from 100 to 250 mcg of compound per milliliter of test media. It can be readily combined in known carriers, adjuvants and vehicles to provide compositions adapted to control or eradicate fungal growth.

The compound of this invention is readily prepared. An illustrative example of its currently preferred preparation is set forth below.

2-Amino-5-benzyloxy-6-Methoxybenzothiazole Hydrochloride

To 2-benzyloxy-1-methoxy-4-aminobenzene (15 g, 0.065 mole) and sodium thiocyanate (21 g, 0.26 mole) in methanol (200 ml) at −10 to −15° was added 250 ml of methanol saturated with sodium bromide and containing 3.6 ml (0.065 mole) of bromine. Addition was carried out over 0.5 hr. and the mixture was then stirred overnight without further cooling. The mixture was concentrated to dryness, and to the residue was added water (500 ml). Dilute ammonium hydroxide (200 ml) was then added, and the resulting solid was collected (16 g). The solid was warmed to 50° in chloroform (400 ml), treated with Norite, and filtered. To the filtrate was added 20 ml of ethanol saturated with hydrogen chloride. The precipitate was collected and recrystallized from 2-propanol to give 9.0 g (43%) of title compound (0.05% overall yield).

Anal. Calcd. for $C_{15}H_{14}N_2O_2S \cdot HCl$: C, 55.81; H, 4.68; N, 8.68; Found: C, 55.55; H, 4.73; N, 8.62

What is claimed is:
1. The compound 2-Amino-5-phenylmethoxy-6-methoxybenzothiazole hydrochloride.